(12) United States Patent
Rossetto (10) Patent No.: US 9,173,706 B2
(45) Date of Patent: Nov. 3, 2015

(54) DUAL-BAND DIPOLE MICROWAVE ABLATION ANTENNA

(75) Inventor: Francesca Rossetto, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1517 days.

(21) Appl. No.: 12/197,473

(22) Filed: Aug. 25, 2008

(65) Prior Publication Data

US 2010/0045558 A1    Feb. 25, 2010

(51) Int. Cl.
    *A61B 18/18*      (2006.01)
    *A61B 18/00*      (2006.01)

(52) U.S. Cl.
    CPC ............. *A61B 18/18* (2013.01); *A61B 18/1815* (2013.01); *A61B 2018/00023* (2013.01)

(58) Field of Classification Search
    CPC .................. A61B 18/18; A61B 18/15; A61B 2018/00011; A61B 2018/00023; A61B 2018/00577; A61B 2018/00732; A61B 2018/1838; A61B 2018/1861; A61B 2018/1869; A61B 2018/1876; A61B 2018/1884; A61B 2018/1892; A61B 18/1815; A61B 2018/183; A61B 2018/1846; A61N 5/045
    USPC ............. 606/42, 33; 600/2, 10; 607/100, 102, 607/154–156
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,583,556 A * | 4/1986 | Hines et al. | 607/116 |
| 4,798,215 A | 1/1989 | Turner | |
| 5,057,106 A | 10/1991 | Kasevich et al. | |
| 5,097,844 A | 3/1992 | Turner | |
| 5,129,396 A | 7/1992 | Rosen et al. | |
| 5,301,687 A * | 4/1994 | Wong et al. | 607/116 |
| 5,323,778 A | 6/1994 | Kandarpa et al. | |
| 5,358,515 A | 10/1994 | Hurter et al. | |
| 5,405,346 A | 4/1995 | Grundy et al. | |
| 5,417,210 A | 5/1995 | Funda et al. | |
| 5,554,176 A * | 9/1996 | Maddison et al. | 607/9 |
| 5,681,282 A | 10/1997 | Eggers et al. | |
| 5,693,082 A | 12/1997 | Warner et al. | |
| 5,957,969 A | 9/1999 | Warner et al. | |
| 6,031,375 A | 2/2000 | Atalar et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Michael Peffley
*Assistant Examiner* — Thomas Giuliani (57) ABSTRACT

A triaxial microwave antenna assembly is disclosed. The triaxial microwave antenna includes a feedline having an inner conductor, a central conductor disposed about the inner conductor and an outer conductor disposed about the central conductor and a radiating portion including a high frequency radiating section and a low frequency radiating section.

9 Claims, 5 Drawing Sheets

(56) References Cited

U.S. PATENT DOCUMENTS

| | | | |
|---|---|---|---|
| 6,375,606 | B1 | 4/2002 | Garibaldi et al. |
| 6,496,738 | B2 | 12/2002 | Carr |
| 6,603,994 | B2 | 8/2003 | Wallace et al. |
| 6,725,080 | B2 | 4/2004 | Melkent et al. |
| 6,950,076 | B2 | 9/2005 | Holly |
| 6,961,028 | B2 | 11/2005 | Joy et al. |
| 6,999,041 | B2 | 2/2006 | Holly |
| 7,101,369 | B2 | 9/2006 | Van Der Weide |
| 7,102,586 | B2 | 9/2006 | Liang et al. |
| 7,244,254 | B2 | 7/2007 | Brace et al. |
| 7,311,703 | B2 | 12/2007 | Turovskiy et al. |
| 7,439,736 | B2 | 10/2008 | Meaney et al. |
| 7,467,015 | B2 | 12/2008 | Van der Weide |
| 7,565,207 | B2 | 7/2009 | Turner et al. |
| 7,933,660 | B2 * | 4/2011 | Carr .............. 607/102 |
| 2002/0022836 | A1 | 2/2002 | Goble et al. |
| 2004/0049254 | A1 * | 3/2004 | Longo .............. 607/116 |
| 2004/0097805 | A1 | 5/2004 | Verard et al. |
| 2004/0242992 | A1 | 12/2004 | Hareyama |
| 2005/0015081 | A1 * | 1/2005 | Turovskiy et al. .............. 606/33 |
| 2005/0149010 | A1 * | 7/2005 | Turovskiy et al. .............. 606/33 |
| 2005/0245919 | A1 * | 11/2005 | van der Welde .............. 606/33 |
| 2006/0293650 | A1 * | 12/2006 | Prakash et al. .............. 606/33 |
| 2006/0293651 | A1 * | 12/2006 | Cronin .............. 606/33 |
| 2006/0293652 | A1 | 12/2006 | Van Der Weide |
| 2007/0016180 | A1 | 1/2007 | Lee, Jr., et al. |
| 2007/0016181 | A1 | 1/2007 | Van Der Weide et al. |
| 2008/0308256 | A1 | 12/2008 | Deborski et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/011049 | 2/2005 |
| WO | WO2005/016119 | 2/2005 |
| WO | WO2007/024878 | 3/2007 |
| WO | WO2007/112081 | 10/2007 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP09010873.9—extended dated Nov. 13, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.

(56) References Cited

OTHER PUBLICATIONS

U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.

(56) References Cited

OTHER PUBLICATIONS

Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MdTech product literature (Mar. 2000) I'D Wire: product description, 1 page.
MdTech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes to Model Electrical Heating and Non•Llnear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971; vol. 217, No. 7, pp. 916-921.
Walt Boyles, "Instrumentation Reference Book", 2002, Butterworth-Heinemann, pp. 262-264.

(56) References Cited

OTHER PUBLICATIONS

European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480:8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One with No Moving Parts", 4 pages, Nov. 1, 2003.

* cited by examiner

“DUAL-BAND DIPOLE MICROWAVE ABLATION ANTENNA”

BACKGROUND

1. Technical Field

The present disclosure relates generally to microwave antennas used in tissue ablation procedures. More particularly, the present disclosure is directed to dipole microwave antennas having dual-band capability.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Conventional microwave antennas operate at a single frequency allowing for creation of similarly shaped lesions (e.g., spherical, oblong, etc.). To obtain a different ablation shape, a different type of antenna is usually used.

SUMMARY

According to another aspect of the present disclosure, a triaxial microwave antenna assembly is disclosed. The triaxial microwave antenna includes a feedline having an inner conductor, a central conductor disposed about the inner conductor and an outer conductor disposed about the central conductor and a radiating portion including a high frequency radiating section and a low frequency radiating section.

A method for forming a lesion is also contemplated by the present disclosure. The method includes the initial step of providing a triaxial microwave antenna assembly that includes a radiating portion. The radiating portion includes a first frequency radiating section having a first predetermined length and a second frequency radiating section having a second predetermined length. The method also includes the step of supplying microwave either at a first frequency or a second frequency to selectively energize at least one of the first frequency radiating section and the second radiating section to adjust at least one property of the lection. The property of the lesion including a depth and a diameter.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
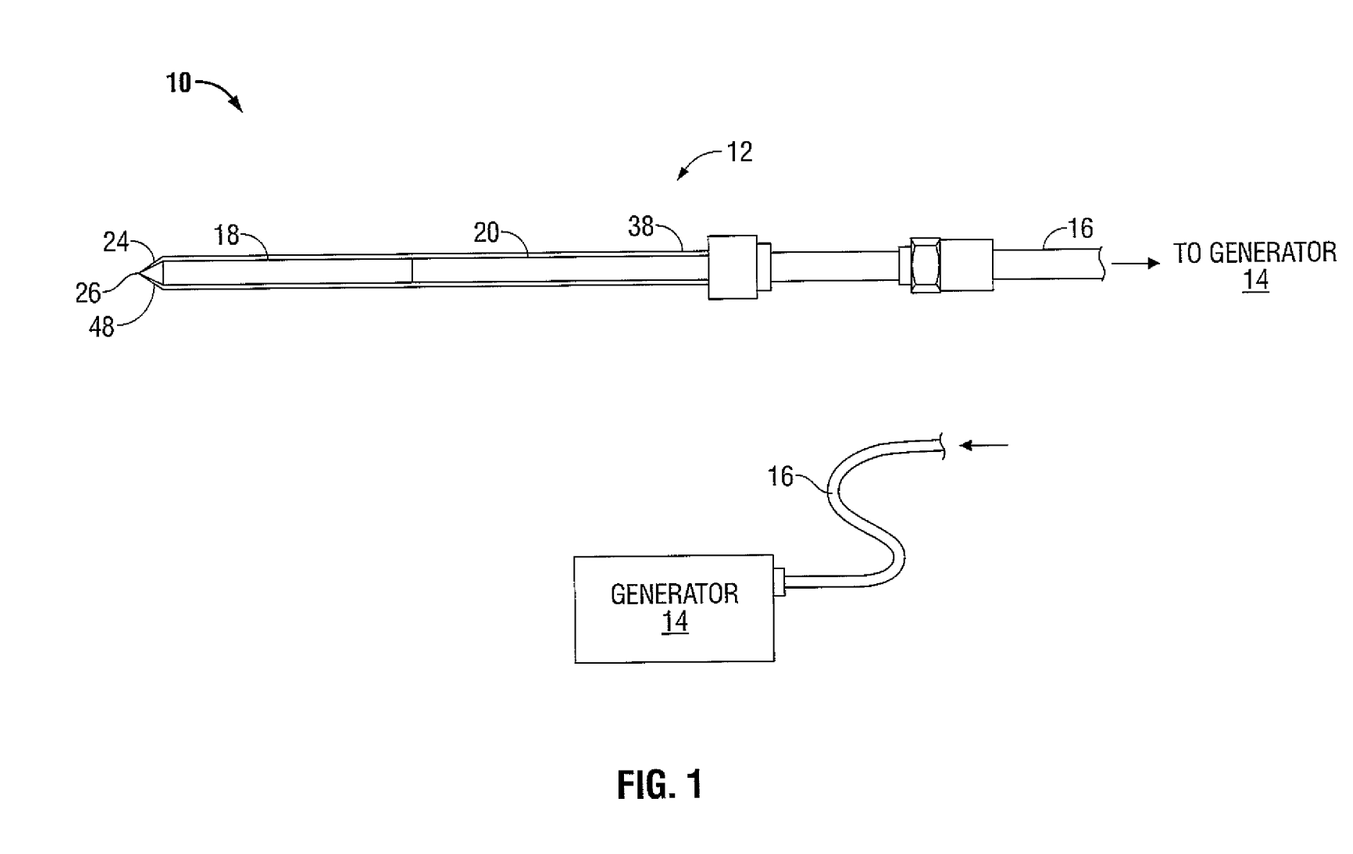
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 5000 MHz.

In the illustrated embodiment, the antenna assembly 12 includes a radiating portion 18 connected by feedline 20 (or shaft) to the cable 16. Sheath 38 encloses radiating portion 18 and feedline 20 allowing a coolant fluid to circulate around the antenna assembly 12. In another embodiment, a solid dielectric material may be disposed therein.

Figure 2:
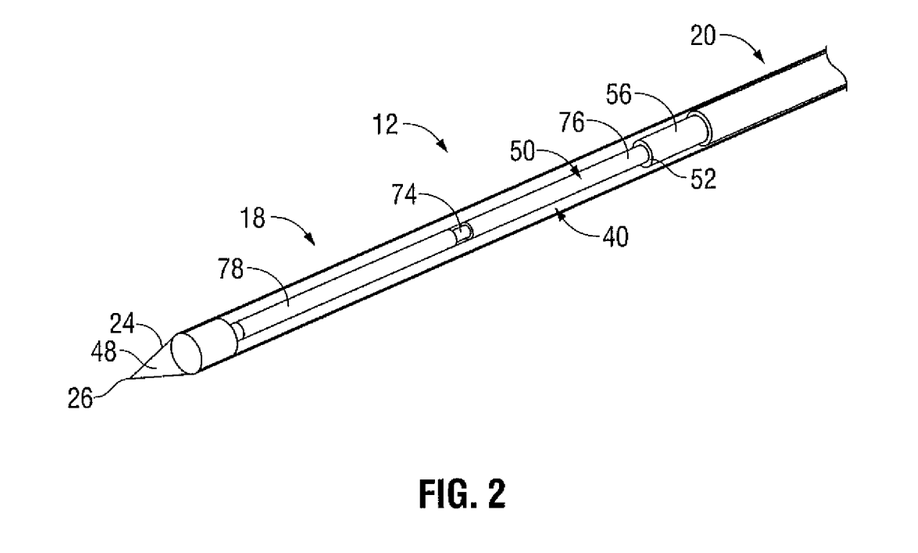
FIG. 2 is a perspective, internal view of the microwave antenna assembly of FIG. 1 according to the present disclosure.
Figure 3:
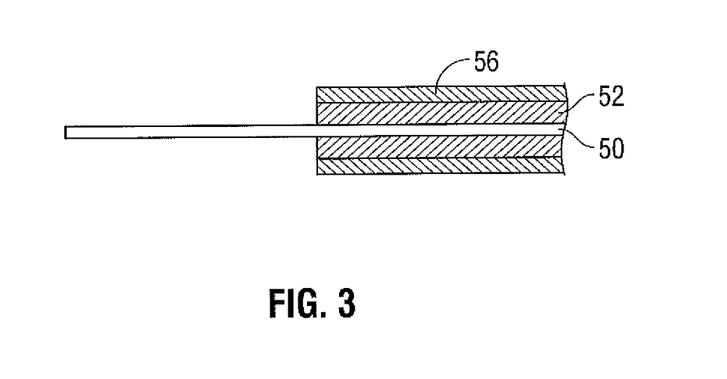
FIG. 3 is a cross-sectional side view of the microwave antenna assembly of FIG. 1 according to the present disclosure.

FIG. 2 illustrates the radiating portion 18 of the antenna assembly 12 having a dipole antenna 40. The dipole antenna 40 is coupled to the feedline 20 that electrically connects antenna assembly 12 to the generator 14. As shown in FIG. 3, the feedline 20 includes an inner conductor 50 (e.g., a wire) surrounded by an inner insulator 52, which is, in turn, surrounded by an outer conductor 56 (e.g., a cylindrical conducting sheath). The inner and outer conductors 50 and 56 may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial semi-rigid or flexible cable having a wire with a 0.047" outer diameter rated for 50 Ohms.

The dipole antenna 40 may be formed from the inner conductor 50 and the inner insulator 52, which are extended outside the outer conductor 56, as shown best in FIG. 2. In one embodiment, in which the feedline 20 is formed from a coaxial cable, the outer conductor 56 and the inner insulator 52 may be stripped to reveal the inner conductor 50, as shown in FIG. 3.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat.

The tip 48, which may be formed from a variety of heat-resistant materials suitable for penetrating tissue, such as metals (e.g., stainless steel) and various thermoplastic materials, such as poletherimide, polyamide thermoplastic resins, an example of which is Ultem® sold by General Electric Co. of Fairfield, Conn. The tip 48 may be machined from various stock rods to obtain a desired shape. The tip 48 may be attached to the distal portion 78 using various adhesives, such as epoxy seal. If the tip 48 is metal, the tip 48 may be soldered or welded to the distal portion 78.

Figure 4:
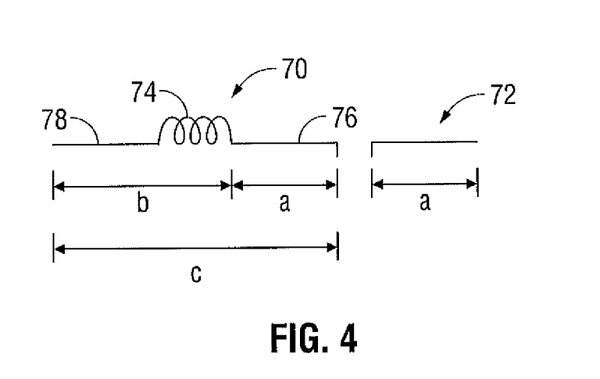
FIG. 4 is a schematic diagram of the microwave antenna assembly of FIG. 1 according to the present disclosure.
Figure 5:
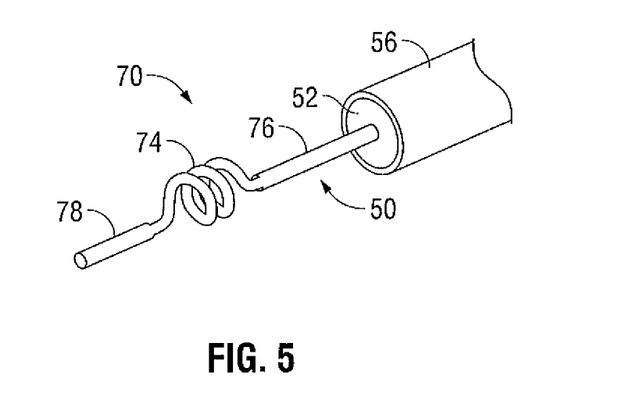
FIG. 5 is an isometric view of a radiating portion of the microwave antenna assembly of FIG. 1 according to the present disclosure.

When microwave energy is applied to the dipole antenna 40, the extended portion of the inner conductor 50 acts as a first pole 70 and the outer conductor 56 acts as a second pole 72, as represented in FIG. 4. As shown in FIG. 5, the first pole 70 includes an inductor 74 that maybe disposed between a proximal portion 76 and a distal portion 78 of the first pole 70. The distal portion 78 and the proximal portion 76 may be either balanced (e.g., of equal lengths) or unbalanced (e.g., of unequal lengths).

The second pole 72 (FIG. 4) may have a first predetermined length a, that may be a quarter wavelength of the operating amplitude of the generator 14 at a first frequency. More specifically, the generator 14 may be adapted to operate at various frequencies, such as first and second frequencies, 2450 MHz and 915 MHz, respectively. Accordingly, the length a may be a quarter wavelength of the amplitude of the microwave energy supplied at 2450 MHz (e.g., $\lambda_{eHF}/4$, wherein HF is the first frequency or the high frequency). Other suitable frequencies are contemplated by the present disclosure.

The proximal portion 76 of the first pole 70 may be substantially the same length, as the second pole 72, namely length a. The distal portion 78 may have a second predetermined length b, such that the total length of the first pole 70 may be length c, which is the sum of the lengths a and b. Length c may be a quarter wavelength of the operational amplitude of the generator 14 at the second frequency, namely 915 MHz (e.g., $\lambda_{eLF}/4$, wherein LF is the second frequency or the low frequency). Those skilled in the art will appreciate that the length of the second pole 72 and the proximal portion 76 as well as the total length of the first pole 70 are not limited to a quarter wavelength of the operating frequency and can be any suitable length maintaining the proportional length relationship discussed herein.

The inductor 74, which may be a meandered strip or any suitable type of inductor, may have an impedance proportional to the frequency of the signal supplied by the generator 14, such that the impedance of the inductor 74 is relatively high when the generator 14 is operating at the first frequency (e.g., 2450 MHz) and lower when the generator 14 is outputting at the second frequency (e.g., 915 MHz).

At the first frequency, the impedance of the inductor 74 is high and, therefore, blocks the high frequency microwave signal from reaching the distal portion 78 of the first pole 70. As a result, the microwave signal energizes the second pole 72 and the proximal portion 76 of the first pole 70, hence only the second pole 72 and the proximal portion 76 resonate. In other words, first operative length (e.g., the total resonating length) of the antenna 40 is going to be the sum of second pole 72 and the proximal portion 76 and is approximately half the wavelength of the operational amplitude of the generator 14 at the first frequency (e.g., $\lambda_{eHF}/4+\lambda_{eHF}/4=\lambda_{eHF}/2$).

At the second frequency, the impedance of the inductor 74 is lower and, therefore, allows for propagation of the lower frequency microwave signal to the distal portion 78. Since the microwave signal energizes the second pole 72 and the first pole 70 in its entirety, the first and second pole 70 and 72 fully resonate. As a result, second operative length (e.g., the total resonating length) length of the antenna 40 is the sum of the second pole 72 and the first pole 70 and is approximately half the wavelength of the operational amplitude of the generator 14 at the second frequency (e.g., $\lambda_{eLF}/4+\lambda_{eHF}/4$).

Since the antenna 40 is resonant at the first and second frequencies, the total length of the first pole 70 and the second pole 72 may be $\lambda_{eLF}/2$, in which case the length of the first pole 70 is not equal to $\lambda_{eLF}/4$. To ensure broadband behavior at both frequencies, a choke is not used. A coolant fluid may be supplied into the sheath 38 (FIG. 1) to limit ablation of tissue along the shaft of the assembly 12.

Figure 6:
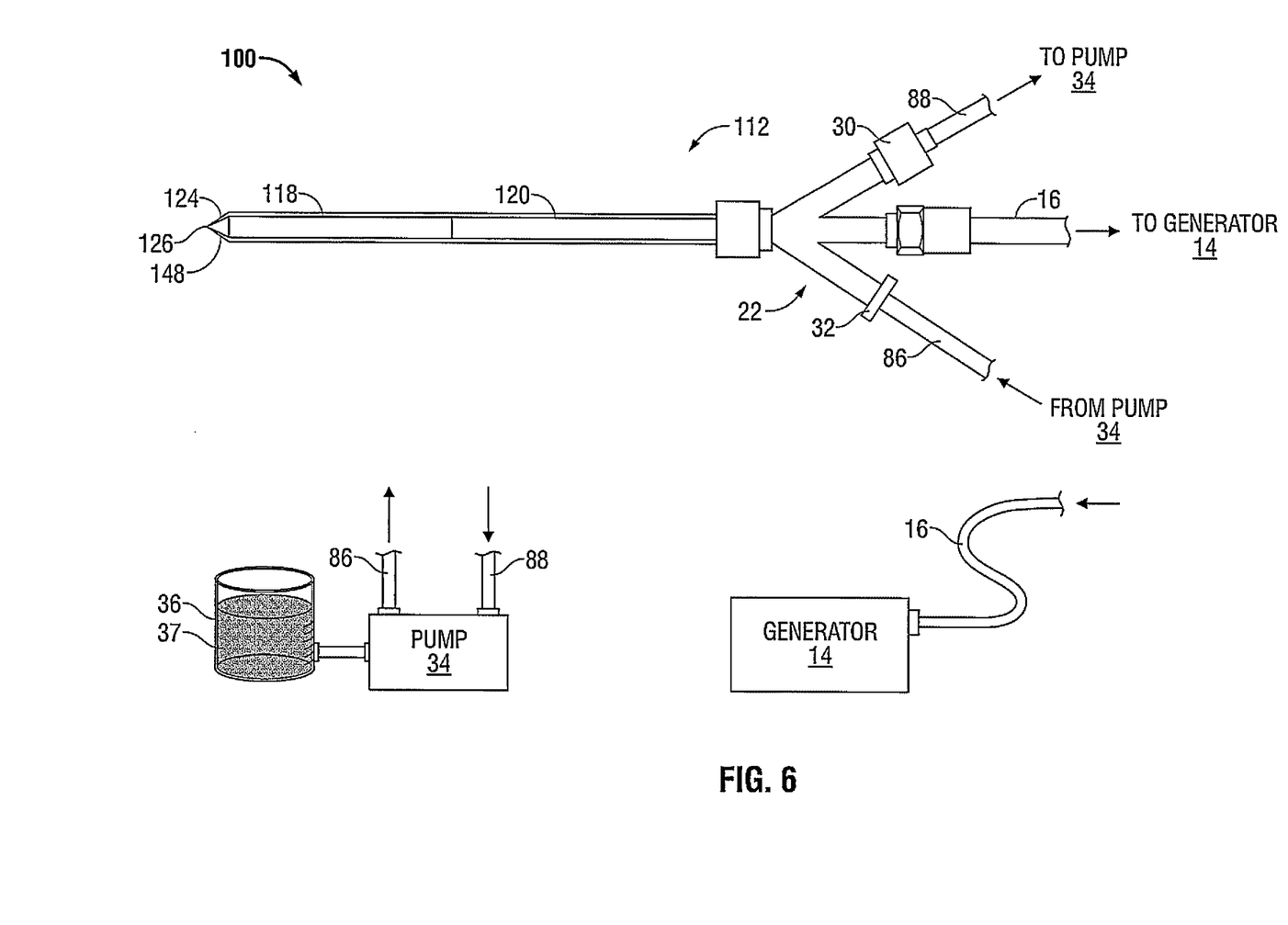
FIG. 6 is a schematic diagram of one embodiment of a microwave ablation system according to an embodiment of the present disclosure.

FIG. 6 shows a microwave ablation system 100 that includes a triaxial microwave antenna assembly 112 coupled to the microwave generator 14 via the flexible coaxial cable 16. The triaxial antenna assembly 112 includes a radiating portion 118 connected by feedline 120 (or shaft) to the cable 16 and a tip 148 having a tapered end 124 that terminates, in one embodiment, at a pointed end 126, similar to tip 48 described above. More specifically, the triaxial antenna assembly 112 is coupled to the cable 16 through a connection hub 22 having an outlet fluid port 30 and an inlet fluid port 32 allowing a coolant fluid 37 to circulate from ports 30 and 32 around the triaxial antenna assembly 112. The coolant fluid 37 may be a dielectric coolant fluid such as deionized water or saline. The ports 30 and 32 are also coupled to a supply pump 34 that is, in turn, coupled to a supply tank 36, via supply lines 86, 88. The supply pump 34 may be a peristaltic pump or any other suitable type. The supply tank 36 stores the coolant fluid 37 and, in one embodiment, may maintain the fluid at a predetermined temperature. More specifically, the supply tank 36 may include a coolant unit which cools the returning liquid from the triaxial antenna assembly 112. In another embodiment, the coolant fluid 37 may be a gas and/or a mixture of fluid and gas.

Figure 7A:
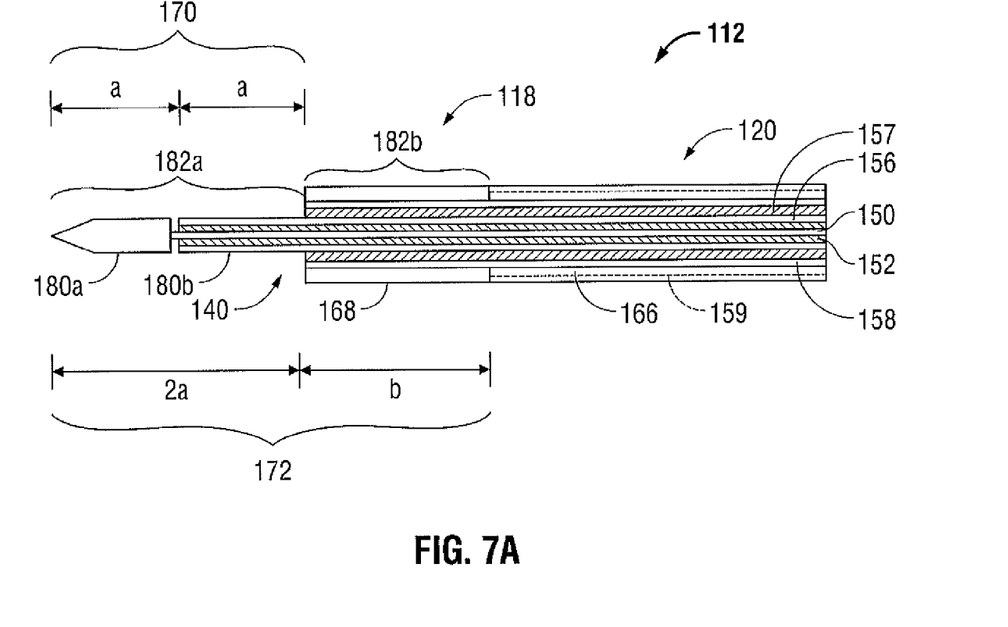
FIGS. 7A and 7B are cross-sectional side views of embodiments of the microwave antenna assembly of FIG. 6 according to the present disclosure.

FIG. 7A illustrates the feedline 120 and the radiating portion 118 of the triaxial antenna assembly 112 having a double-dipole antenna 140. The double-dipole antenna 140 is coupled to the feedline 120 that electrically connects the triaxial antenna assembly 112 to the generator 14. The radiating portion 118 includes an inner conductor 150 (e.g., a wire) surrounded by an inner insulator 152, which is surrounded by a central conductor 156 (e.g., a cylindrical conducting sheath). The radiating portion 118 also includes a central insulator 157 disposed around the central conductor 156, which is surrounded by an outer conductor 158. The inner, central and outer conductors 150, 156 and 158, respectively, may be constructed of copper, gold, stainless steel or other conductive metals with similar conductivity values. Much like the aforementioned conductors, the metals may be plated with other materials, e.g., other conductive materials, to improve their properties, e.g., to improve conductivity or decrease energy loss, etc.

The outer conductor 158 may be surrounded by an outer jacket 159 defining a cavity 166 therebetween. In one embodiment, the outer jacket 159 may be hollow and may include the cavity 166 inside thereof. The cavity 166 is in liquid communication with the ports 30 and 32 (see FIG. 6) for circulating the coolant fluid 37 therethrough. The outer conductor 158 may also include a solid conducting portion 168 disposed at the distal end thereof. The circulation of the coolant fluid 37 through the entire length of the cavity 166 that covers the feedline 120 removes the heat generated during ablation.

The triaxial antenna assembly 112 is adapted to deliver microwave energy at two distinct frequencies (e.g., high frequency and low frequency). The inner and central conductors 150 and 156 represent the first dipole 170 of the double-dipole antenna 140, and are adapted to deliver microwave energy at a first frequency (e.g., 2450 MHz). The first dipole 170 and the outer conductor 158 represent the second dipole 172 of the double-dipole antenna 140 and are adapted to deliver microwave energy at a second frequency (e.g., 915 MHz). Thus, the central conductor 156 serves a dual purpose in the triaxial antenna assembly 112—the central conductor 156 acts as an outer conductor for the inner conductor 150 during high frequency energy delivery and as an inner conductor for the outer conductor 158 during low frequency energy delivery.

The inner conductor 150 extends outside the central conductor 156 by a first predetermined length a, which may be a quarter wavelength of the amplitude of the microwave energy supplied at 2450 MHz (e.g., $\lambda_{eHF}/4$, wherein HF is the first frequency or the high frequency). The central conductor 156 also extends outside the outer conductor 158 by the predetermined length a. During application of high frequency energy the exposed sections of the inner and central conductors 150 and 156 define a high frequency radiating section 170 having a total length equal to the sum of lengths a (e.g., $\lambda_{eHF}/2$). More specifically, during application of high frequency microwave energy, the inner conductor 150 acts as a high frequency first pole 180a and the central conductor 156 acts as a high frequency second pole 180b for the first dipole 170 of the double-dipole antenna 140.

In the embodiment illustrated in FIG. 7A, the cooling cavity 166 extends from the proximal end of the conducting portion 168 along the feedline 120, covering the outer conductor 158. During application of low frequency energy, conductors 150 and 156 along with conducting portion 168 define a low frequency radiating section 172 having a total length of 2a+b. The length b may be any length suitable such that the sum of 2a+b represents a half wavelength of the amplitude of the microwave energy supplied at the low frequency (e.g., 915 MHz). During application of low frequency energy, the inner and central conductors 150 and 156 act as a low frequency first pole 182a, and the conducting portion 168 acts as a low frequency second pole 182b for the second dipole of the double-dipole antenna 140.

Figure 7B:
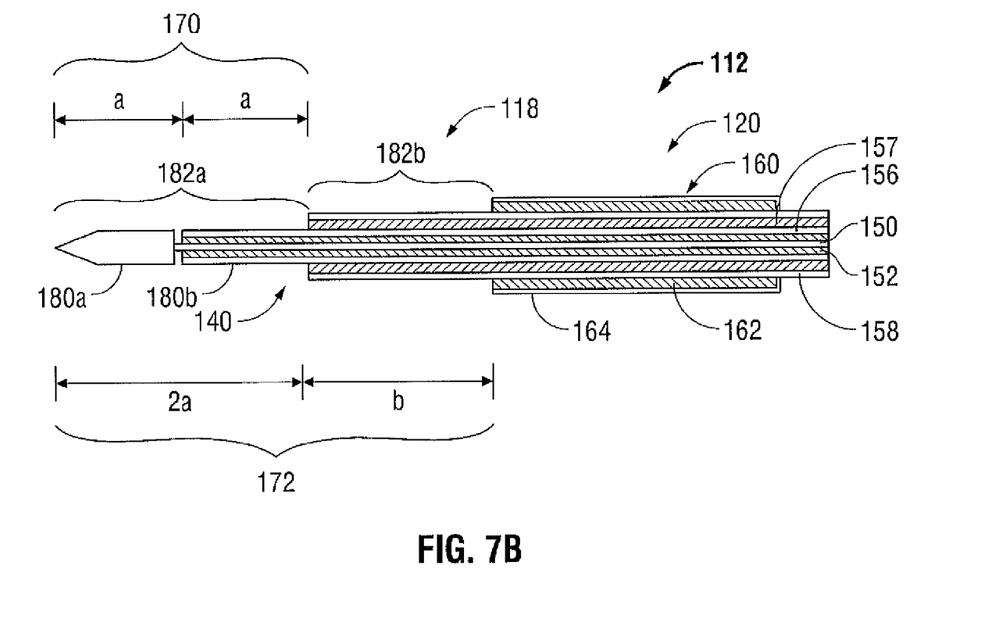

With reference to FIG. 7B, the triaxial antenna assembly 112 may include a choke 160 that is disposed around the outer conductor 158. Choke 160 may include an inner dielectric layer 162 and an outer conductive layer 164. The choke 160 may be a quarter-wavelength shorted choke at the low frequency and is shorted to the outer conductor 158 at the proximal end of the choke 160 by soldering or other suitable methods. The choke 160 may replace the cooling cavity 166, and defines a portion of the radiating section 118 as a low frequency radiating section 172. More specifically, the choke 160 is disposed a second predetermined distance, length b, from the distal end of the outer conductor 158. Length b may be such that the sum of 2a+b represents half wavelength of the amplitude of the microwave energy supplied at 915 MHz (e.g., $\lambda eLF/2$, wherein LF is the second frequency or the low frequency). The choke 160 is adapted to limit the bandwidth of the microwave energy only at the second frequency and does not interfere with the application of microwave energy at the first frequency.

During application of low frequency microwave energy, the inner and central conductors 150 and 156 act as a low frequency first pole 182a and a distal portion of the outer conductor 158 acts as a low frequency second pole 182b. The low frequency second pole 182b may have a length b such that in conjunction with the low frequency first pole 182a, the first and second poles 182a and 182b define a low frequency radiating section 172 having a total length equal to the sum of lengths 2a+b (e.g., $\lambda_{eLF}/2$).

The dual-frequency operation of the antenna assembly 12 and the triaxial antenna assembly 112 allows for the production of lesions of varying shape and depth. More specifically, the total operative length (e.g., the resonating portion) of the antenna 40 of the assembly 12 (FIG. 2) may be controlled by adjusting the frequency of the output of the generator 14. Since the depth of the lesion produced by the antenna 40 is directly related to the length of the resonating portion of the antenna 40, adjusting the relevant portions of the antenna 40 that resonate allows a user to control of the shape (e.g., diameter) and depth of the desired lesion. In other words, by varying the frequency of the microwave signal supplied to the antenna 40 the shape of the lesion is controlled accordingly by nature of the inductor 74 disposed on the first pole 70 (FIG. 5). The inductor 74 controls the operative length of the antenna 40 based on the frequency of the microwave energy supplied to the antenna 40.

A method for forming a lesion is also contemplated by the present disclosure. The method includes the steps of supplying microwave energy at a predetermined frequency (e.g., first or second frequency) to the microwave antenna assembly 12 and adjusting the operative length of the dipole antenna 40 based on the frequency of the microwave energy supplied thereto to adjust at least one property (e.g., depth, circumference, shape, etc.) of the lesion.

With respect to the triaxial antenna assembly 112 of FIG. 6, the depth of the desired lesion may also be varied. By applying the microwave energy at a low frequency (e.g., 915 MHz) the energy passes through the outer conductor 158 and the central conductor 156 thereby generating a lesion along the entire low frequency radiating section 172. When applying microwave at a high frequency (e.g., 2450 MHz) the energy passes through the inner and central conductors 150 and 156, thereby generating a lesion only along the high frequency radiating section 170. As shown in FIGS. 7A and 7B, energizing either or both sections 170 and 172 allows a user to generate varying depth lesions.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A triaxial microwave antenna assembly comprising:
   a feedline including an inner conductor, a central conductor disposed about the inner conductor and an outer conductor disposed about the central conductor, wherein each of the inner conductor, central conductor, and outer conductor is insulated from each other; and
   a dual dipole antenna having a radiating portion including a first dipole configured to radiate microwave energy supplied to the radiating portion at a first frequency and a second dipole configured to radiate microwave energy supplied to the radiating portion at a second frequency; and a choke disposed around the outer conductor at a distance of a half wavelength of the microwave energy supplied at the second frequency from a distal end of the inner conductor, the choke configured to only limit the microwave energy supplied to the radiating portion at the second frequency.

2. The triaxial microwave antenna assembly according to claim 1, wherein the first dipole includes a portion of the inner conductor and a portion of the central conductor and the second dipole includes the portion of the central conductor and a portion of the outer conductor.

3. The triaxial microwave antenna assembly according to claim 2, wherein the portion of the inner conductor extends a first predetermined distance from the central conductor and the portion of the central conductor extends the first predetermined distance from the outer conductor.

4. The triaxial microwave antenna assembly according to claim 3, wherein the first predetermined distance is a quarter wavelength of the microwave energy supplied at the first frequency.

5. The triaxial microwave antenna assembly according to claim 3, wherein the outer conductor includes a tubular structure defining a cavity therein configured to circulate a coolant fluid therethrough, wherein the cavity is disposed a second predetermined distance from the distal portion of the outer conductor.

6. The triaxial microwave antenna assembly according to claim 5, wherein the sum of twice the first predetermined distance and the second predetermined distance is a half wavelength of the microwave energy supplied at the second frequency.

7. The triaxial microwave antenna assembly according to claim 3, wherein the choke is disposed a second predetermined distance from the distal portion of the outer conductor.

8. The triaxial microwave antenna assembly according to claim 7, wherein the sum of twice the first predetermined distance and the second predetermined distance is a half wavelength of the microwave energy supplied at the second frequency.

9. The triaxial microwave antenna assembly according to claim 1, wherein the choke is shorted to the outer conductor.

* * * * *